United States Patent
Bartholomaeus et al.

(10) Patent No.: US 7,572,463 B2
(45) Date of Patent: *Aug. 11, 2009

(54) ORAL DOSAGE FORMS

(75) Inventors: Johannes Bartholomaeus, Aachen (DE); Iris Ziegler, Rott-Roetgen (DE)

(73) Assignee: Gruenenthal GmbH, Aachen (DE)

( * ) Notice: Subject to any disclaimer, the term of this patent is extended or adjusted under 35 U.S.C. 154(b) by 308 days.

This patent is subject to a terminal disclaimer.

(21) Appl. No.: 10/084,674

(22) Filed: Feb. 28, 2002

(65) Prior Publication Data

US 2002/0176888 A1 Nov. 28, 2002

Related U.S. Application Data

(63) Continuation of application No. PCT/EP00/08402, filed on Aug. 29, 2000.

(30) Foreign Application Priority Data

| Aug. 31, 1999 | (DE) | ................................ 199 40 740 |
| Aug. 31, 1999 | (DE) | ................................ 199 40 944 |
| May 16, 2000 | (DE) | ................................ 100 23 699 |

(51) Int. Cl.
*A61K 9/22* (2006.01)

(52) U.S. Cl. ...................... 424/468; 424/400; 424/464; 424/465

(58) Field of Classification Search ................ 424/464, 424/489, 465, 451, 490, 484, 400, 469, 470, 424/471, 472, 474; 514/646
See application file for complete search history.

(56) References Cited

U.S. PATENT DOCUMENTS

| 5,478,577 | A | * | 12/1995 | Sackler et al. ............... 424/489 |
| 5,601,842 | A | * | 2/1997 | Bartholomaeus ............ 424/464 |
| 5,776,492 | A | * | 7/1998 | Betzing et al. ............... 424/465 |
| 5,811,126 | A | * | 9/1998 | Krishnamurthy ............ 424/498 |
| 6,322,819 | B1 | * | 11/2001 | Burnside et al. ............. 424/494 |
| 6,451,350 | B1 | * | 9/2002 | Bartholomaeus et al. .... 424/490 |
| 6,558,701 | B2 | * | 5/2003 | Bartholomaeus et al. .... 424/472 |
| 6,558,704 | B1 | * | 5/2003 | Bartholomaeus et al. .... 424/489 |
| 6,576,260 | B2 | * | 6/2003 | Bartholomaeus et al. .... 424/469 |
| 6,709,678 | B2 | * | 3/2004 | Gruber ........................ 424/490 |

FOREIGN PATENT DOCUMENTS

| EP | 0065123 | | 4/1982 |
| EP | 0192909 | | 12/1985 |
| WO | 94/05277 | | 3/1994 |
| WO | WO 99/01111 | * | 1/1999 |
| WO | WO9901111 | * | 1/1999 |

* cited by examiner

*Primary Examiner*—D. L Jones
(74) *Attorney, Agent, or Firm*—Crowell & Moring LLP

(57) ABSTRACT

A controlled-release oral dosage formulation of a salt-forming active ingredient, wherein the active ingredient is present as at least two different salts in a solid aggregation state, wherein the two different salts have different water solubility and release the active ingredient in-vitro at different release rates, provided that oral dosage formulations are excluded which comprise a resin carrying a sulfonate group and a resin carrying a carboxyl group and which contain an active ingredient in a form fixed to these resins.

65 Claims, 5 Drawing Sheets

ORAL DOSAGE FORMS

CROSS REFERENCE TO RELATED APPLICATIONS

The present application is a continuation of international patent application no. PCT/EP00/04802, filed Aug. 29, 2000, designating the United States of America, the entire disclosure of which is incorporated herein by reference. Priority is claimed based on German patent application nos. 199 40 944.7, filed Aug. 31, 1999; 199 40 740.1, filed Aug. 31, 1999; and 100 23 699.5, filed May 16, 2000.

BACKGROUND OF THE INVENTION

The present invention relates to oral dosage forms with controlled total-release of an active substance, wherein the same active substance is present in the form of at least two different salts which are present in the dosage form in a solid aggregation state and which have a different in-vitro release of this active substance.

Administration of an active substance in the form of preparations, from which this active substance is released in a controlled manner, is advantageous for many therapies. For example, the controlled release of an active substance with a relatively short half-life will prolong its availability in the body. Moreover, uniform blood levels can be adjusted in this manner; any undesirable accompanying symptoms may, optionally, be minimised; and observance of dosage specifications can be improved.

Conventionally, the controlled release of an active substance from oral dosage forms can be achieved only through relatively expensive formulation procedures, such as coating the oral dosage forms containing active substances with a retarding film coating or embedding the active substances in a retarding matrix. If a different release of partial quantities of an active substance is required in order to control the overall release profile, the same active substance or the same active-substance salt may be processed separately to provide different formulations, which may then be combined, for example, as a retarded and a non-retarded form of one dosage form.

SUMMARY

One object of the present invention was therefore to provide oral dosage forms of an active substance from which this active substance is released in a controlled manner without the need for expensive, separate formulation stages to adjust the overall release profile of the active substance from a dosage form.

BRIEF DESCRIPTION OF THE DRAWINGS

Features and advantages of the present invention will become apparent to those skilled in the art from the following description with reference to the drawings. in which.

DETAILED DESCRIPTION OF THE INVENTION

Figure 1:
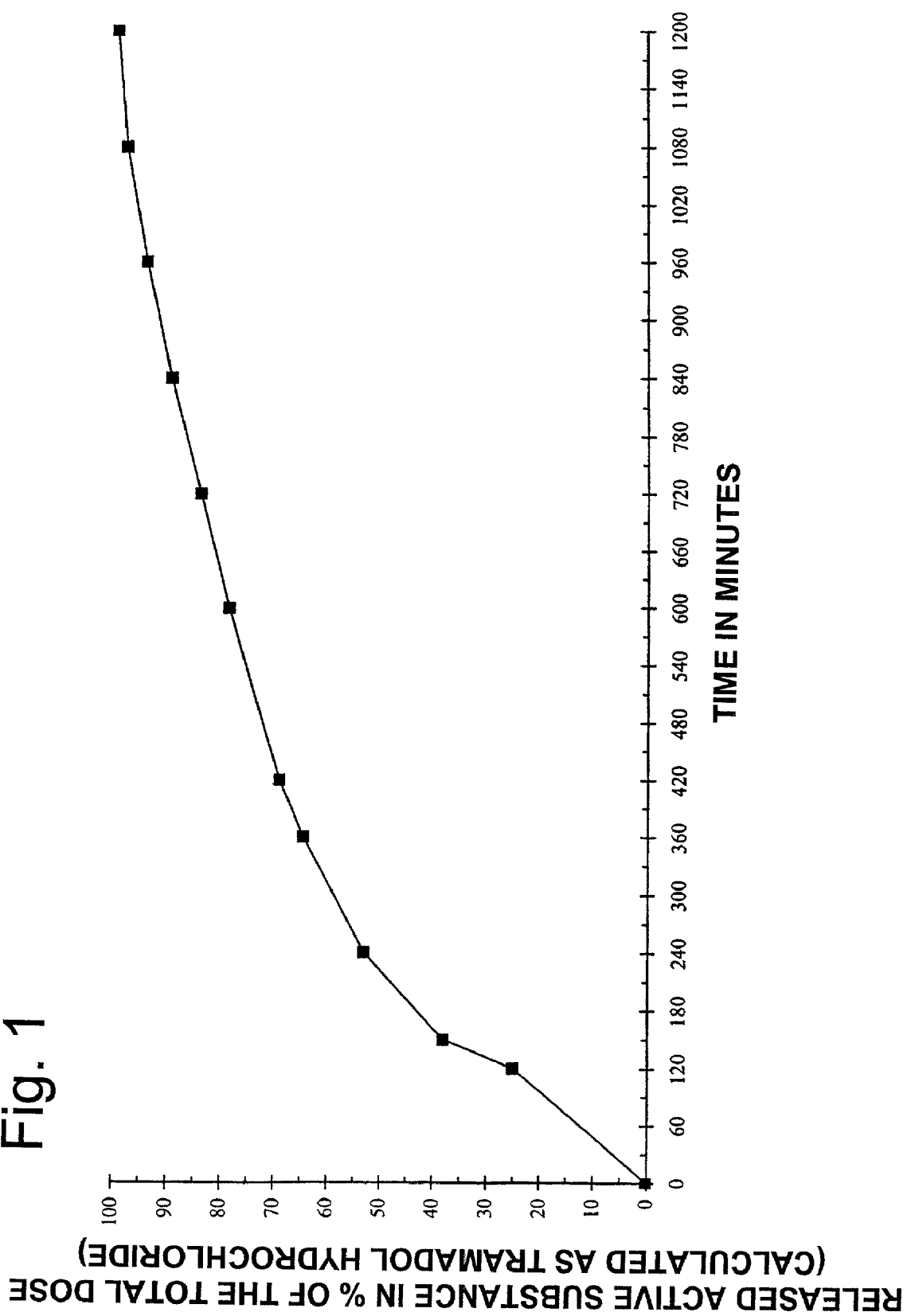
FIG. 1 shows a release profile relevant to Example 1.

According to the invention, this object is achieved by providing oral dosage forms with controlled total-release of an active substance, in which the same active substance is present in the form of at least two different salts, which are present in the dosage form in the solid aggregation state and which have a different in-vitro release of this active substance.

In one preferred embodiment of the present invention, all of the various salts of the active substance in one dosage form have a mutually different water solubility, which, in principle, leads to a different rate of dissolution of the active substance.

Preferably, the water solubilities of each of the various active-substance salts used in the dosage form according to the invention differ from one another at least by a factor of 2.

In the case of the oral dosage forms according to the invention, the total-release profile for the relevant active substance can be adjusted to the required form by selecting the active-substance salts and their quantitative proportions in the combined dosage form. This allows therapy-specific adjustment of the plasma level of an active substance, for example, the achievement of as stable a plasma level as possible over a relatively long period; or a pulsed release with time-displaced plasma level peaks of the active substance; or the achievement of a plasma level of the active substance relative to the circadian rhythms of the body.

In the sense of the present invention, an active substance is any substance, which exerts an influence on biological, biochemical, chemical, physical or physiological processes or structures in the human or animal body, and which can form a solid salt at 25° C. by conversion with an acid or a base.

This formation of active-substance salts may also be achieved through conversion with another active substance with the corresponding acidic or basic function.

Preferably, the salt-forming active substance is selected from the group of the salt-forming, pharmaceutically active substances, vitamins, nutrients, minerals or diagnostic agents, particularly preferably from the group of salt-forming, pharmaceutically active substances.

If the active substance is a salt-forming pharmaceutically active substance, it may preferably be a salt-forming member of the following group of substances: analgesics, anthelmintics, anti-arrhythmics, anti-asthmatics, antidepressants, antidiabetics, antidotes, anti-allergics, antitussives, antibiotics, anti-emetics, anti-infectives, antihistamines, antihypertonics, antihypertensives, anticoagulants, antirheumatics, antipyretics, anxiolytics, slimming drugs, drugs for treatment of acidosis, drugs for treatment of vertigo, antihaemorrhagics, antifibrinolytics, haemostatics, antihypoglycaemics, antihypotonics, antimycotics, antiphlogistics, expectorants, antiepileptics, drugs for treatment of arteriosclerosis, beta-adrenoceptor blockers, calcium-channel blockers, renin-angiotensin inhibitors, broncholytics, cholagogues, biliary tract therapeutics, cholinergics, corticoids (internal), circulation-stimulating drugs, detoxification drugs, geriatric drugs, gout treatments, anti-influenza drugs, cold treatments, gynaecological drugs, hepatic drugs, hypnotics, hormones such as pituitary gland hormones, hypothalamic hormones, regulatory peptides or their inhibitors, immunomodulators, cardiac drugs, analeptics, antihypoxaemics, anti-anaemics, antidementia drugs (nootropics), appetite suppressants, coronary drugs, laxatives, chemotherapeutics, diuretics, enzymes, fungistatics, lipid-lowering drugs, neural therapeutics, gastrointestinal drugs, anti-migraine drugs, muscle relaxants, anti-neuropathy drugs, neurotropic drugs, neuroleptics, drugs for treatment of osteoporosis, calcium metabolism regulators, anti-parkinsonian drugs, drugs for treatment of extrapyramidal symptoms, psychoactive drugs, roborants, tonics, thyroid drugs, sex hormones or their inhibitors, spasmolytics, thrombocyte aggregation inhibitors, anti-tuberculosis drugs, urologics, vein-therapeutics, antineoplastic drugs or protectives, sedatives, vasodilators, virustatics or cytostatics. Particularly preferably, the salt-forming pharmaceutically active substance is selected from the group of salt-forming analgesics, anti-infectives or neuroleptics.

Salt-forming opioids, compounds with an opioid action, or non-steroidal analgesics may be used preferably as salt-forming analgesics.

As salt-forming opioids or compounds with opioid action, the following may be present preferably: brifentanil, carfentanil, fentatienil, lofentanil, ocfentanil, trefentanil, codeine, dextropropoxyphene, dihydrocodeine, diphenoxylate, meptazinol, nalbuphine, pethidine (meperidine), tilidine, tramadol, viminol, butorphanol, dextromoramide, dezocine, diacetylmorphine (heroin), hydrocodone, hydromorphone, ketobemidone, levomethadone, levomethadyl, levorphanol, morphine, nalorphine, oxycodone, pentazocine, piritramide, alfentanil, buprenorphine, etorphine, fentanyl, remifentanil or sufentanil. Particularly preferably, tramadol or morphine may be used.

Promethazine may be used preferably as a salt-forming neuroleptic.

Physiologically acceptable active-substance salts may be present as the active-substance salts in the oral, pharmaceutical dosage forms according to the invention. A further active substance may be used as a partner salt to the active substance used.

Preferably, these salts are selected from the group of: chloride, bromide, sulfate, sulfonate, phosphate, tartrate; theoclate, embonate, formiate, acetate, propionate, benzoate, oxalate, succinate, citrate, diclofenacate, naproxenate, salicylate, glutamate, fumarate, acetylsalicylate, aspartate, glutarate, stearate, butyrate, malonate, lactate, mesylate, saccharinate, cyclamate or acesulfamate. Particularly preferably, these salts may be selected from the group of chloride, sulfate, saccharinate, theoclate, embonate, diclofenacate, naproxenate or salicylate.

Preferably, tramadol hydrochloride, tramadol saccharinate and tramadol diclofenacate or morphine hydrochloride, morphine saccharinate and morphine sulfate may be present alongside one another as salts of the same active substance in the oral dosage forms according to the invention. Particularly preferably, tramadol hydrochloride and tramadol saccharinate or tramadol hydrochloride and tramadol diclofenacate may be present alongside one another as salts of the same active substance in the oral dosage forms according to the invention.

An alkali metal salt, alkaline-earth metal salt, ammonium salt, iron salt or aluminium salt of the active substance may be used with equal preference as the active-substance salt; particularly preferably an alkali metal salt, most particularly preferably the sodium or potassium salt of the active substance may be present.

The controlled, total-release of the active substance from the oral dosage forms according to the invention can additionally be modified in that at least one of the active-substance salts, preferably several to all the active-substance salts, may be present in the dosage forms in retarded form. Equally preferably, the oral dosage form can be retarded with the combined formulation of all active-substance salts to provide the dosage form according to the invention.

In one preferred embodiment of the present invention, retardation is provided by a retarding coating and/or by embedding in a retarding matrix.

The retarding coating is preferably based on a water-insoluble, optionally modified, natural or synthetic polymer, optionally in combination with a conventional softener on a natural, semi synthetic or synthetic wax or fat or fatty alcohol or a mixture of at least two of the above-named components.

Regarding the water-insoluble polymers for the manufacture of a retarding coating, the following are preferably used as a coating material: polymethacrylate, particularly preferably poly($C_{1-4}$)-alkyl(meth)acrylate, poly($C_{1-4}$)-dialkylamino-($C_{1-4}$)-alkyl(meth)acrylate and/or their copolymers, preferably ethylacrylate/methylmethacrylate-copolymer with a molar ratio of the monomers of 2:1 (Eudragit NE30D®), ethylacrylate/methylmethacrylate/trimethylammonium ethylmethacrylate-chloride-copolymer with a molar ratio of the monomers of 1:2:0.1 (Eudragit RS®), ethylacrylate/methylmethacrylate/trimethylammonium ethylmethacrylate-chloride-copolymer with a molar ratio of the monomers of 1:2:0.2 (Eudragit RL®), or a mixture of at least two of the above-named polymers.

These coating materials are available commercially as 30 wt. % aqueous latex dispersions, i.e. as Eudragit RS30D®, Eudragit NE30D® and Eudragit RL30D® and are also used as such for the preferred coating material.

With equal preference, polyvinyl acetates, optionally in combination with further auxiliary substances, may be used as water-insoluble polymers for the manufacture of the retarding coating for the dosage forms according to the invention as a whole or for the individual active-substance salts. These are available commercially as an aqueous dispersion containing 27 wt. % polyvinyl acetate, 2.5 wt. % povidone and 0.3 wt. % sodium lauryl sulfate (Kollicoat SR 30 D®).

The retarding coatings may also be based on water-insoluble cellulose derivatives, preferably alkyl celluloses such as, e.g. ethyl cellulose, or cellulose esters, such as, e.g. cellulose acetate. The coatings made from ethyl cellulose are preferably applied from an aqueous, pseudo-latex dispersion. Aqueous ethyl cellulose dispersions are available commercially as 30 wt. % dispersions (Aquacoat®) or as 25 wt. % dispersions (Surelease®).

With reference to semi synthetic or synthetic waxes, fats and/or fatty alcohols, the retarding coating may preferably be based upon carnauba wax, beeswax, glycerine monostearate, glycerine monobehenate (Compritol ATO888®), glycerine ditripalmitostearate (Precirol ATO5®), microcrystalline wax, cetyl alcohol, cetyl stearyl alcohol or a mixture of at least two of these components.

If the retarding coating is based on a water-insoluble, optionally modified, natural and/or synthetic polymer, the coating dispersion or solution may have, alongside the corresponding polymers, a conventional, physiologically acceptable, softener known to a person skilled in the art, in order to lower the necessary minimum film temperature or to modify the properties of the film.

Appropriate softeners include, for example, lipophilic diesters made from an aliphatic or aromatic dicarboxylic acid with $C_6$-$C_{40}$ and an aliphatic alcohol with $C_1$-$C_8$, such as dibutylphthalate, diethylphthalate, dibutyl sebacate or diethyl sebacate, hydrophilic or lipophilic esters of citric acid, such as triethyl citrate, tributyl citrate, acetyltributyl citrate or acetyltriethyl citrate, polyethylene glycols, propylene glycol, esters of glycerine, such as triacetin, Myvacet® (acetylated mono- and digylcerides, $C_{23}H_{44}O_5$ to $C_{25}H_{47}O_7$), mid-chain trigylcerides (Miglyol®), oleic acid or mixtures of at least two of the named softeners.

Preferably, triethyl citrate is used as a softener for aqueous dispersions of Eudragit RS® and optionally Eudragit RL®.

Preferably, the retarding coating contains the softener(s) in quantities of 5 to 50 wt. %, particularly preferably 10 to 40 wt. % and most particularly preferably 10 to 30 wt. % relative to the quantity of the polymer(s) used. In individual cases, for example, for cellulose acetate, larger quantities of softeners, preferably up to 110 wt. % may also be used.

Furthermore, the retarding coating may have other conventional auxiliary substances known to a person skilled in the art, such as slip agents, preferably talcum or glycerine monostearate, colouring pigments, preferably iron oxides or titanium dioxide, surfactants, such as Tween 80® or auxiliary substances for modulation of the film properties, such as water-soluble pore-formers, e.g., lactose, polyethylene glycol 1000 (PEG 1000) or saccharose.

The oral dosage forms according to the invention may also contain at least one active-substance salt, preferably several to all active-substance salts, in a retarding matrix, preferably evenly distributed. Physiologically acceptable, hydrophilic materials known to a person skilled in the art may preferably be used as matrix materials. Particularly preferably, the retarding matrix is based on cellulose ethers, cellulose esters, and/or acrylic resins, most particularly preferably on ethyl cellulose, hydroxypropylmethyl cellulose, hydroxypropyl cellulose, hydroxymethyl cellulose, poly(meth)acrylic acid and/or their salts, amides and/or esters.

Equally preferably, physiologically acceptable, hydrophobic materials known to a person skilled in the art may be used as matrix materials. Particularly preferably, the matrix is based on hydrophobic polymers, waxes, fats, long-chained fatty acids, fatty alcohols or corresponding esters or ethers or their mixtures, and particularly preferably on mono-or diglycerides of $C_{12}$-$C_{30}$ fatty acids and/or $C_{12}$-$C_{30}$ fatty alcohols and/or waxes or their mixtures.

It is also possible to use mixtures of the above-named hydrophilic and hydrophobic materials as the retarding matrix material.

If the oral dosage forms according to the invention contain active-substance salts of which the acid component is a weaker acid than the hydrochloric acid occurring in the stomach of the human or animal body, these should have a protective coating, which is preferably resistant to gastric juices. This protective coating can ensure that the active substance in the active-substance salts present in the oral dosage forms according to the invention is released either in a retarded manner or not at all in the stomach. Gastric juice-resistant coatings ensure that the oral dosage forms according to the invention pass through the gastric tract un-dissolved and the active substance is not released until it reaches the intestinal tract. Preferably, the gastric juice-resistant coating dissolves at a pH value from 5 to 7.5. The required total-release profile can accordingly be monitored and adjusted by a person skilled in the art by simple, preliminary in-vitro experiments with the assistance of known measuring methods for determining the release of the active substance.

A gastric juice-resistant coating preferably consists of methacrylic acid/methylmethacrylate copolymers with a molar ratio of the monomers of 1:1 (Eudragit L®), methacrylic acid/methylmethacrylate copolymers with a molar ratio of the monomers of 1:2 (Eudragit S®), methacrylic acid/ethylacrylate copolymers with a molar ratio of the monomers of 1:1 (Eudragit L30-D55®), methacrylic acid/methylacrylate/methylmethacrylate with a molar relationship of the monomers of 7:3:1 (Eudragit FS®), shellac, hydroxypropylmethyl cellulose acetate succinate, cellulose acetate phthalate or a mixture of at least two of these components, optionally also in combination with poly(meth)acrylates, preferably Eudragit NE30D® and/or Eudragit RL® and/or Eudragit RS®.

The coating dispersion or solution from which the gastric juice-resistant coating is applied, may have one of the above-named softeners in addition to the corresponding polymers.

Furthermore, the retarding coating materials listed above may also be applied, as a protective coating against the gastric acids, in various thicknesses, which are known to a person skilled in the art.

The retarding and/or protective coatings of the oral dosage forms according to the invention may be applied according to the conventional processes appropriate for the relevant coating which are also known to a person skilled in the art, such as, by spraying the solutions, dispersions or suspensions, by fusion processes or by powder application processes. The solutions, dispersions or suspensions may be used in the form of aqueous or organic solutions or dispersions. In this context, aqueous dispersions are preferably used. Alcohols, for example, ethanol or isopropanol, ketones, such as acetone, esters, such as ethylacetate, chlorinated hydrocarbons, such as dichloromethane may be used as organic solvents, whereby alcohols and ketones are used preferably. It is also possible to use mixtures of at least two of the above-named solvents.

These processes are known from the prior art, e.g. H. Sucker, Georg Thieme Verlag, 1991, pp 347 ff. They are listed here as a reference and therefore apply as a component of the disclosure.

In one preferred embodiment of the present invention, the oral dosage forms according to the invention are present in the form of tablets, chewable tablets, chewing gums, coated tablets or powders, optionally filled into capsules, but particularly preferably in the form of tablets.

In a further preferred embodiment of the present invention, the oral dosage forms according to the invention are present in multi-particulate form, preferably in the form of micro-tablets, micro-capsules, granulates, active-substance crystals or pellets, particularly preferably in the form of micro-tablets, granulates or pellets, optionally filled into capsules or compressed to form tablets.

If the oral dosage forms according to the invention are present in the form of granulates or pellets, these may preferably have a size within the range of 0.1 to 3 mm, particularly preferably within the range from 0.5 to 2 mm.

If the oral dosage forms according to the invention are present in the form of micro-tablets, these may preferably have a diameter within the range of 0.5 to 5 mm, particularly preferably within the range from 1 to 3 mm, and most particularly preferably within the range from 1 to 2 mm.

If the oral dosage forms according to the invention are present in the form of active substance crystals, micro-particles, micro-pellets or micro-capsules, these may preferably have a diameter within the range of 10 µm to 1 mm, particularly preferably within the range from 15 µm to 0.5 mm, and most particularly preferably within the range from 30 µm to 200 µm.

Moreover, the oral dosage forms according to the invention may, depending on the design, contain the conventional auxiliary substances known to a person skilled in the art.

If the oral dosage forms according to the invention are present in the form of tablets or micro-tablets, these may contain as additional auxiliary substances preferably micro-crystalline cellulose, cellulose ether, lactose, starch and starch derivatives, sugar alcohols, calcium hydrogen phosphate and the other conventional binding agents, flow-regulators, slip agents and, optionally, dispersion agents known to a person skilled in the art.

If the oral dosage forms according to the invention are present in the form of pellets, granulates or micro-pellets, these may contain as additional auxiliary substances preferably micro-crystalline cellulose, cellulose ether, lactose, starch and starch derivatives, sugar alcohols, calcium hydrogen phosphate, fatty alcohols, esters of glycerine or fatty acid esters.

If the oral dosage forms according to the invention are present in the form of micro-capsules or micro-particles, these may, depending on the type of process used for their manufacture, contain the conventional auxiliary substances known to a person skilled in the art.

For the manufacture of the oral dosage forms according to the invention, the active-substance salts and optionally additional auxiliary substances are preferably homogenised in a high-speed mixer or in a rotary fluidised bed. Following this, the formulation is carried out according to the various methods known to a person skilled in the art, and optionally, the preferably gastric juice-resistant protective coating is applied from the above-named coating materials in accordance with the methods indicated above.

If the oral dosage forms according to the invention are present in the form of tablets, the various solid, active-substance salts are preferably homogenised, processed by means of wet, dry or fusion granulation to form granulates, and compressed to form tablets or manufactured by direct tabletting of the active-substance salts, optionally with additional auxiliary substances. Moreover, the tablets may preferably be manufactured by compression of optionally coated pellets, active-substance crystals, micro-particles or micro-capsules.

Oral dosage forms according to the invention in the form of pellets may preferably be manufactured by mixing the active-substance salts, extrusion and spheronisation, by agglomeration pelletisation or by direct pelletisation in a high-speed mixer or in the rotary fluidised bed. Manufacture of the pellets by extrusion of wet compounds and subsequent spheronisation is particularly preferred.

The manufacture of micro-capsules is carried out according to conventional micro-encapsulation processes, such as spray-drying, spray-hardening or coacervation.

If the oral dosage forms according to the invention are present in multi-particulate form, the retarding coating is preferably applied in such a manner that the multi-particulate forms containing the salts of the active substance are coated, after their manufacture, with the relevant polymers and, optionally, additional auxiliary substances from aqueous and/or organic media, preferably from aqueous media, with the assistance of the fluidised-bed process, and the coating is preferably dried at the same time at conventional temperatures in the fluidised bed, without subsequent curing of the coating. In the case of poly(meth)acrylate coatings, the coating is preferably dried with an inlet-air temperature within the range of 30-50° C., preferably within the range 35 to 45° C.

For coatings based on cellulose, such as ethyl cellulose or cellulose acetate, drying is preferably carried out at a temperature in the range 50 to 80° C., particularly preferably within the range 55 to 65° C.

Wax coatings can be applied by fusion-coating in the fluidised bed and cooling after coating until completely hardened at temperatures below the relevant fusion range. Wax coatings can also be applied by spraying their solutions in organic solvents.

The quantity of the active substance to be administered to the patient varies in dependence upon the type of active substance used, upon the weight of the patient, the therapeutic indication and, optionally, also on the severity of the pain and/or the disease.

Preferably the quantity of active substance to be administered and its total-release from the salts of the active substance should be adjusted in such a manner that administration of the oral dosage forms according to the invention is required at most twice, preferably only once daily.

The oral dosage forms according to the invention have the advantage that the active substance can be released in a controlled manner in accordance with the desired total-release profile, e.g. in a pulsatile or multiple-phase manner over the given period, without the need for expensive, separate formulation stages for the active substance.

This means that the time and therefore also the cost for the manufacture of the oral dosage forms according to the invention can be minimised.

The water solubility of the active-substance salts was determined as follows:

The relevant active-substance salt was added to deionised water at 25° C. in a quantity sufficient to provide a saturated solution at this temperature (e.g. for tramadol saccharinate approximately 1 g to 10 ml deionised water), which remained saturated after 20 hours stirring at 25° C. The quantity of the relevant active-substance salts required for this may optionally be determined by means of preliminary experiments.

After the un-dissolved active-substance salt had been allowed to settle, the clear supernatant was removed by pipette and centrifuged at rate of at least 3000 rpm for five minutes.

A portion of the clear supernatant obtained in this manner was transferred to the HPLC sample tube and the concentration of the active-substance salt was determined against an appropriate standard.

The release profiles of the oral dosage forms according to the invention were determined as follows:

The dosage forms according to the invention were tested in the European Pharmacopoeia basket apparatus at a temperature of the released medium of 37±0.5° C., and at a rate of 50 rpm for 2 hours in 600 ml synthetic gastric juices without enzymes at pH 1.2. Following this, the dosage form was tested for a further 8 hours in 900 ml synthetic intestinal juices without enzymes at pH 7.2. The quantity of active substance released at a given time was determined in each case by means of HPLC. The values shown are average values based in each case on 3 samples. The invention will be explained below with reference to examples. The explanations are merely exemplary and do not restrict the general idea of the invention.

EXAMPLES

Example 1

Manufacture of the pellets:

50 mg tramadol hydrochloride, 280 g [1e-(m-methoxyphenyl)-2e-dimethylaminomethyl-cyclohexane-1(a)-ol]-[2-(2', 6'-dichloranilino)-phenylacetate] (tramadol diclofenacate) and 330 g microcrystalline cellulose (Avicel PH 101®, FMC) are homogenised in Kenwood Chef Mixer for 10 minutes and then granulated with an adequate quantity of demineralised water to obtain a granulate suitable for extrusion and spheronisation. The wet granulate is extruded in a NICA E140 Extruder with a 1.0×2.0 mm extrusion template and the wet extrudate is spheronised in a NICA Spheroniser Type S450. The pellets are then dried for 24 hours at 50° C. in the drying cabinet. The yield of pellets with a particle size in the range from 800 to 1250 μm obtained through screen fractionation is ≧90%.

Application of the coating:

500 g of these pellets (800 to 1250 μm) are coated in the fluidised bed (Hüttlin HKC05) with the aqueous dispersion of the composition described below with inlet-air temperature of 40° C. up to a weight increase of 7.6% (relative to the starting weight of the pellets).

Aqueous dispersion for 500 g pellets.

| | |
|---|---:|
| Polymethacrylic acid methylmethacrylate (30% aqueous dispersion, Eudragit L30D ®, Röhm) | 100.0 g |
| Triethyl citrate | 6.0 g |
| Glycerine monostearate | 1.8 g |
| Demineralised water | 82.2 g |
| Total: | 190.0 g |

The solubility of the [1e-(m-methoxyphenyl)-2e-dimethylaminomethyl-cyclohexane-1(a)-ol]-[2-(2',6'-dichloranilino)-phenyl acetate] was determined according to the above method at approximately 0.3 mg/ml; the solubility of the tramadol hydrochloride was determined at >300 mg/ml.

In each case, 710 mg of the coated pellets are filled into hard gelatine capsules of size 0 EL using a Zanasi E6 hardgelatine capsule machine.

The release profile was determined according to the method indicated above using the basket apparatus and this is reproduced in the following Table 1 and in FIG. 1 (as a percentage of the total dose, calculated as tramadol hydrochloride). By way of deviation from the conditions described above, the coated pellets were tested for 18 hours in synthetic intestinal juices without enzymes at pH 7.2.

TABLE 1

| Time (minutes) | Tramadol released in mg (calculated as tramadol hydrochloride) |
|---:|---:|
| 0 | 0 |
| 120 | 50 |
| 150 | 76 |
| 240 | 106 |
| 360 | 129 |
| 420 | 138 |
| 600 | 157 |
| 720 | 168 |
| 840 | 179 |
| 960 | 188 |
| 1080 | 195 |
| 1200 | 198 |

710 mg of the gastric juice-resistant coated pellets contain 50 mg tramadol hydrochloride and 280 mg [1e-(m-methoxyphenyl)-2e-dimethylaminomethyl-cyclohexane-1(a)-ol]-[2-(2',6'-dichloranilino)-phenyl acetate] which is equivalent to a total quantity of active substance of 200 mg tramadol hydrochloride.

Example 2

Manufacture of the pellets:

50 mg tramadol hydrochloride, 280 g [1e-(m-methoxyphenyl)-2e-dimethylaminomethyl-cyclohexane-1(a)-ol]-[2-(2',6'-dichloranilino)-phenyl acetate], 120 g lactose monohydrate, 90 g microcrystalline cellulose (Avicel PH 101®, FMC) and 90 g colloidal microcrystalline cellulose (Avicel RC 591®, FMC) are homogenised in a Kenwood Chef Mixer for 10 minutes and then granulated with an adequate quantity of demineralised water to obtain a granulate suitable for extrusion and spheronisation. The wet granulate is extruded in a NICA E140 Extruder with a 1.0×2.0 mm extrusion template and the wet extrudate is spheronised in a NICA Spheroniser Type S450. The pellets are then dried for 24 hours at 50° C. in the drying cabinet. The yield of pellets with a particle size in the range from 800 to 1250 μm obtained through screen fractionation is ≧90%.

Application of the coating:

500 g of these pellets (800 to 1250 μm) are coated in the fluidised bed (Hüttlin HKC05) with an aqueous dispersion of the composition described below with inlet-air temperature of 60° C. up to a weight increase of 2.4% (relative to the starting weight of the pellets).

Aqueous dispersion for 500 g pellets:

| | |
|---|---:|
| Ethyl cellulose (Aquacoat ® ECD30, FMC) | 34.0 g |
| Dibutylsebacate | 2.0 g |
| Tween 80 ® | 0.01 g |
| Anti-foaming emulsion (Fluka) | 0.01 g |
| Demineralised water | 64.0 g |
| Total: | 100.02 g |

Figure 2:
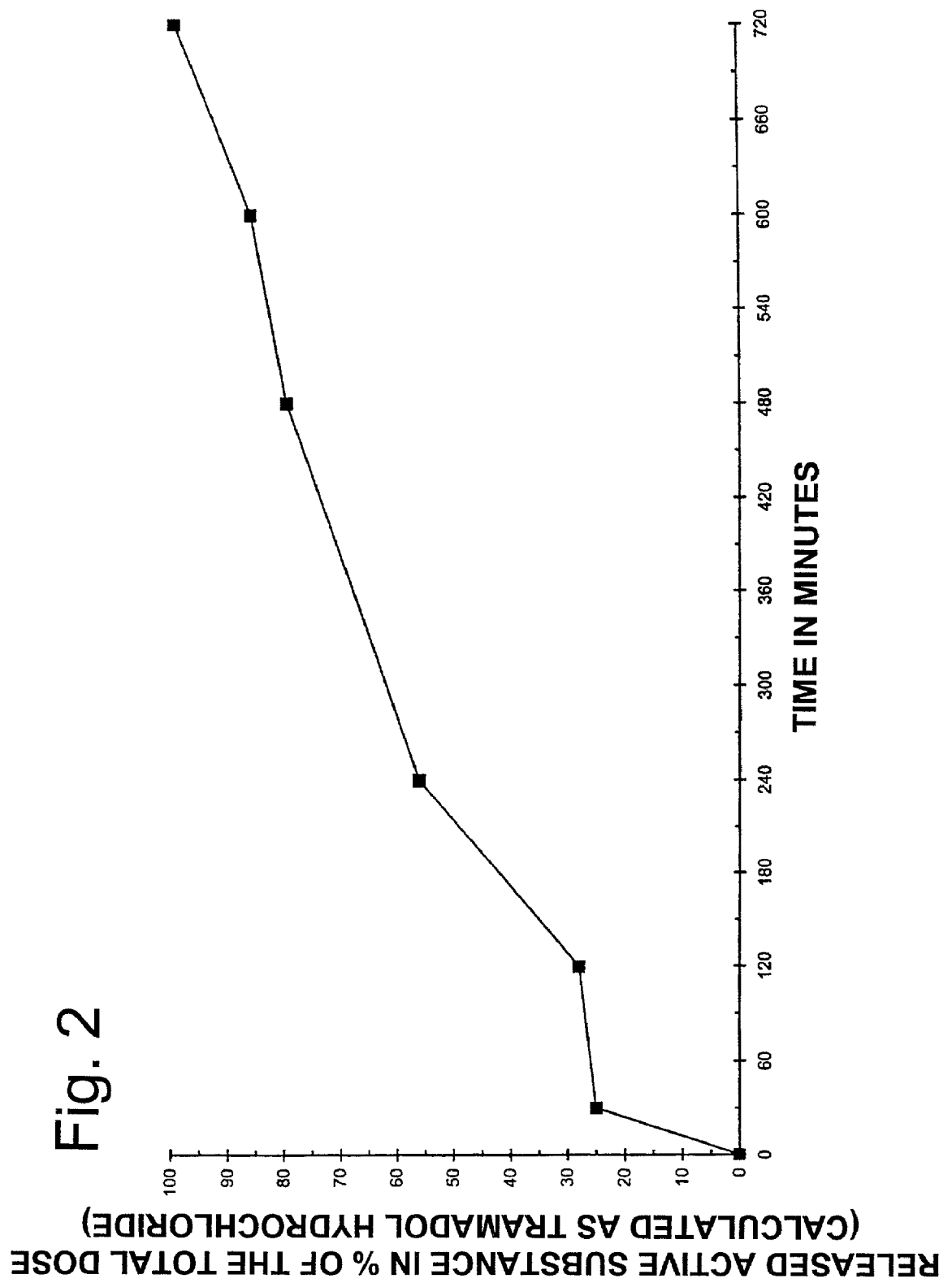
FIG. 2 shows a release profile relevant to Example 2.

The release profile was determined according to the method indicated above using the basket apparatus and this is reproduced in the following Table 2 and in FIG. 2 (as a percentage of the total dose, calculated as tramadol hydrochloride). By way of deviation from the conditions described above, the coated pellets were tested for 10 hours in synthetic intestinal juices without enzymes at pH 7.2.

TABLE 2

| Time (minutes) | Tramadol released in mg (calculated as tramadol hydrochloride) |
|---:|---:|
| 0 | 0 |
| 30 | 25 |
| 120 | 28 |
| 240 | 56 |
| 480 | 79 |
| 600 | 85 |
| 720 | 98 |

323 mg of the coated pellets contain 25 mg tramadol hydrochloride and 140 mg [1e-(m-methoxyphenyl)-2e-dimethylaminomethyl-cyclohexane-1(a)-ol]-[2-(2',6'-dichloranilino)-phenyl acetate] which is equivalent to a total quantity of active substance of 100 mg tramadol hydrochloride.

The ethyl cellulose coating applied does not bring about a retardation of the active-substance salts, but merely ensures that the [2-(2',6'-dichloranilino)-phenyl acetate ion is not driven out of its salt by the gastric acid. The active substance tramadol is released very rapidly from the very readily water-soluble tramadol hydrochloride; the tramadol is released in a retarded manner over a period of 10 hours from the substantially less readily soluble 1e-(m-methoxyphenyl)-2e-dimethylaminomethyl-cyclohexane-1(a)-ol]-[2-(2',6'-dichloranilino)-phenyl acetate.

Example 3

Manufacture of the pellets:

20 mg tramadol hydrochloride, 188 g [1e-(m-methoxyphenyl)-2e-dimethylaminomethyl-cyclohexane-1(a)-ol]-[2-(2', 6'-dichloranilino)-phenyl acetate], 84 g lactose monohydrate and 332 g microcrystalline cellulose (Avicel PH 101®, FMC) are homogenised in a Kenwood Chef Mixer for 10 minutes and then granulated with an adequate quantity of demineralised water to obtain a granulate suitable for extrusion and spheronisation. The wet granulate is extruded in a NICA E140 Extruder with a 1.0×2.0 mm extrusion template and the wet extrudate is spheronised in a NICA Spheroniser Type S450. The pellets are then dried for 24 hours at 50° C. in the drying cabinet. The yield of pellets with a particle size in the range from 800 to 1000 μm obtained through screen fractionation is ≧90%.

Application of the coating:

500 of these pellets (800 to 1000 μm) are coated in the fluidised bed (Hüttlin HKC05 with the aqueous dispersion of the composition described below with inlet-air temperature of 40° C. up to a weight increase of 5.3% (relative to the starting weight of the pellets).

Aqueous dispersion for 500 g pellets:

| | |
|---|---|
| Aqueous shellac solution (ASL 125, 20% solid content) | 125.0 g |
| Triethyl citrate | 1.25 g |
| Demineralised water | 48.75 g |
| Total: | 175.0 g |

Figure 3:
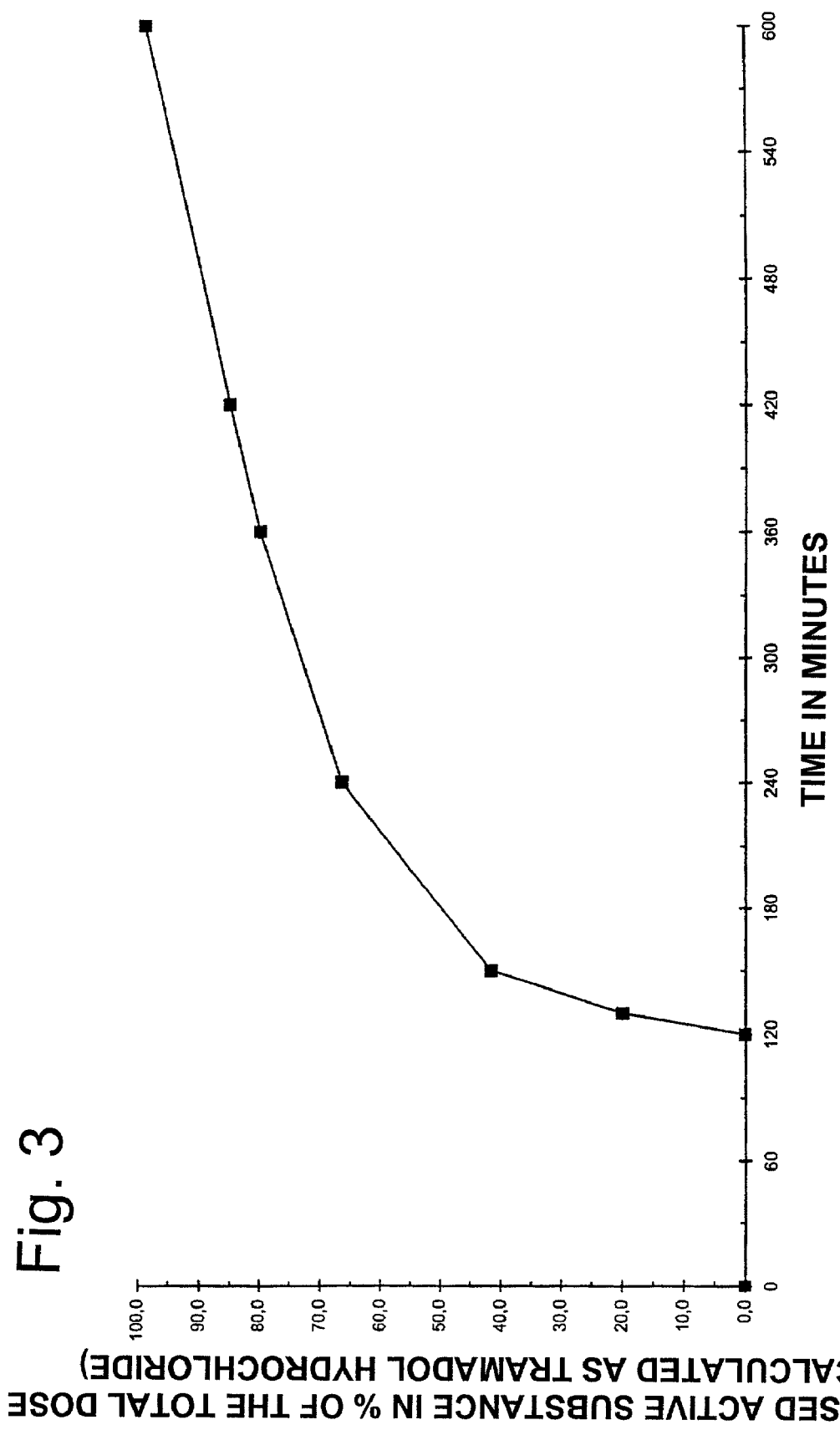
FIG. 3 shows a release profile relevant to Example 3.

The release profile was determined according to the method indicated above using the basket apparatus and this is reproduced in the following Table 3 and in FIG. 3 (as a percentage of the total dose, calculated as tramadol hydrochloride).

TABLE 3

| Time (minutes) | Tramadol released in mg (calculated as tramadol hydrochloride) |
|---|---|
| 0 | 0 |
| 120 | 0 |
| 130 | 12 |
| 150 | 25 |
| 240 | 40 |
| 360 | 48 |
| 420 | 51 |
| 600 | 59 |

219 mg of the gastric juice-resistant coated pellets contain 10 mg tramadol hydrochloride and 94 mg 1e-(m-methoxyphenyl)-2e-dimethylaminomethyl-cyclohexane-1(a)-ol]-[2-(2',6'-dichloranilino)-phenyl acetate which is equivalent to a total quantity of active substance of 60 mg tramadol hydrochloride.

The gastric juice-resistant coating applied ensures that the active substance tramadol is not released during testing in synthetic gastric juices. During tests in synthetic intestinal juices, the active substance tramadol is released very rapidly from the tramadol hydrochloride; the tramadol is released in a retarded manner over a period of 8 hours from 1e-(m-methoxyphenyl)-2e-dimethylaminomethyl-cyclohexane-1 (a)-ol]-[2-(2',6'-dichloranilino)-phenyl acetate.

Example 4

Manufacture of the pellets:

30 mg tramadol hydrochloride, 254 g tramadolsaccharinate (water-solubility, approx. 20 mg/ml, determined according to the method indicated above), and 284 g microcrystalline cellulose (Avicel PH 101®, FMC) are homogenised in a Kenwood Chef Mixer for 10 minutes and then granulated with an adequate quantity of demineralised water to obtain a granulate suitable for extrusion and spheronisation. The wet granulate is extruded in a NICA E140 Extruder with a 1.0×2.0 mm extrusion template and the wet extrudate is spheronised in a NICA Spheroniser Type S450. The pellets are then dried for 24 hours at 50° C. in the drying cabinet. The yield of pellets with a particle size in the range from 800 to 1250 μm obtained through screen fractionation is ≧90%.

Application of the coating:

500 g of these pellets (800 to 1250 μm) are coated in the fluidised bed (Hüttlin HKC05) with the aqueous dispersion of the composition described below with inlet-air temperature 40° C. up to a weight increase of 15% (relative to the starting weight of the pellets).

Aqueous dispersion for 500 g pellets:

| | |
|---|---|
| Ethyl acrylate-methylmethacrylate-trimethyl ammonium ethylmethacrylate chloride copolymer with a ratio of monomers of 1:2:0.1 (30% aqueous dispersion, Eudragit RS30D®, Röhm) | 156 g |
| Ethylacrylate-methylmethacrylate-trimethyl ammonium ethylmethacrylate chloride copolymer with a ratio of monomers of 1:2:0.2 (30% aqueous dispersion, Eudragit RL30D®, Röhm) | 44 g |
| Triethyl citrate | 12 g |
| Glycerine monostearate | 3 g |
| Demineralised water | 160.0 g |
| Total: | 375.0 g |

Figure 4:
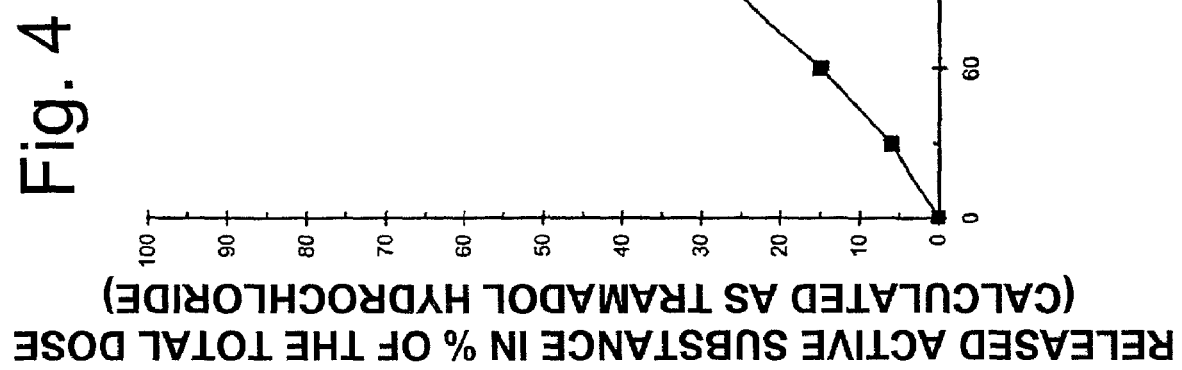
FIG. 4 shows a release profile relevant to Example 4.

The release profile was determined according to the method indicated above using the basket apparatus and this is reproduced in the following Table 4 and in FIG. 4 (as a percentage of the total dose, calculated as tramadol hydrochloride):

TABLE 4

| Time (minutes) | Tramadol released in mg (calculated as tramadol hydrochloride) |
|---|---|
| 0 | 0 |
| 30 | 6 |
| 60 | 15 |
| 120 | 36 |
| 180 | 47 |
| 240 | 58 |
| 360 | 81 |
| 480 | 95 |
| 600 | 99 |

327 mg of the gastric juice-resistant coated pellets contain 15 mg tramadol hydrochloride and 127 mg tramadol saccharinate which is equivalent to a total quantity of active substance of 100 mg tramadol hydrochloride.

Example 5

Manufacture of the pellets:

50 mg tramadol hydrochloride, 526 g tramadolsaccharinate and 384 g microcrystalline cellulose (Avicel PH 101®, FMC) are homogenised in Kenwood Chef Mixer for 10 minutes and then granulated with an adequate quantity of demineralised water to obtain a granulate suitable for extrusion and spheronisation. The wet granulate is extruded in a NICA E140 Extruder with a 1.0×2.0 mm extrusion template and the wet extrudate is spheronised in a NICA Spheroniser Type S450. The pellets are then dried for 24 hours at 50° C. in the drying cabinet. The yield of pellets with a particle size in the range from 800 to 1250 μm obtained through screen fractionation is ≧90%.

Application of the coating:

500 g of these pellets (800 to 1250 μm) are coated in the fluidised bed (Hüttlin HKC05) with the aqueous dispersion of the composition described below with inlet-air temperature 40° C. up to a weight increase of 14.4% (relative to the starting weight of the pellets).

Aqueous dispersion for 500 g pellets:

| | |
|---|---:|
| Ethyl acrylate-methylmethacrylate-trimethyl ammonium ethylmethacrylate chloride copolymer with a ratio of monomers of 1:2:0.1 (30% aqueous dispersion, Eudragit RS30D ® , Röhm) | 177.0 g |
| Polyethylene glycol 6000 (BASF) | 5.3 g |
| Triethyl citrate | 10.6 g |
| Glycerine monostearate | 3.0 g |
| Demineralised water | 164.1 g |
| Total: | 360.0 g |

Figure 5:
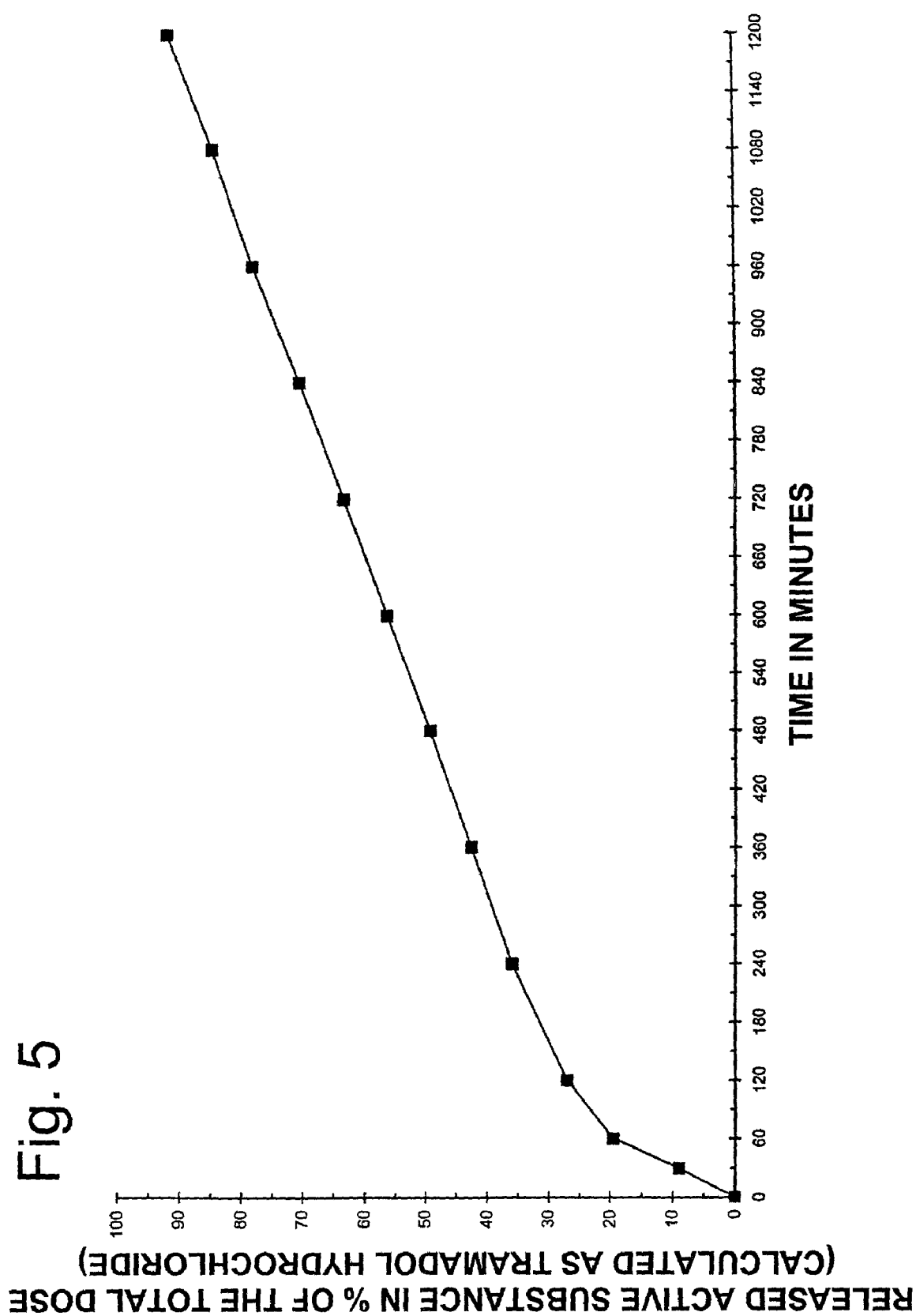
FIG. 5 shows a release profile relevant to Example 5.

The release profile was determined according to the method indicated above using the basket apparatus and this is reproduced in the following Table 5 and in FIG. 5 (as a percentage of the total dose, calculated as tramadol hydrochloride):

TABLE 5

| Time (minutes) | Tramadol released in mg (calculated as tramadol hydrochloride) |
|---:|---:|
| 0 | 0 |
| 30 | 18 |
| 60 | 39 |
| 120 | 54 |
| 240 | 72 |
| 360 | 85 |
| 480 | 98 |
| 600 | 112 |
| 720 | 126 |
| 840 | 140 |
| 960 | 155 |
| 1080 | 168 |
| 1200 | 182 |

549 mg of the gastric juice-resistant coated pellets contain 25 mg tramadol hydrochloride and 263 mg tramadolsaccharinate which is equivalent to a total quantity of active substance of 200 mg tramadol hydrochloride.

Example 6

Manufacture of the tablets:

15 g promethazine hydrochloride, 39 g promethazine theoclate, 120 g microcrystalline cellulose, 75 g methylhydroxypropyl cellulose (50 mPa.s, Metolose 60 SH), 2.5 g highly disperse silicon dioxide and 2.5 g magnesium stearate are homogenised for 10 minutes in a tumbling mixer (Bohle, LM 40). This mixture is compressed on a Korsch EK0 Eccentric Press with a stamping tool to obtain round, convex tablets with a diameter of 9 mm.

The release profile was determined according to the method indicated above. By way of deviation from the conditions described above, the coated tablets were tested in the blade mixer apparatus described in the European Pharmacopoeia.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A controlled-release oral dosage formulation of a salt-forming active ingredient, wherein the active ingredient is present as at least two different salts in a solid aggregation state from which the active ingredient is released by dissolution of said salts, wherein the two different salts have different water solubility and release the active ingredient in-vitro at different release rates, provided that oral dosage formulations are excluded which comprise a resin carrying a sulfonate group and a resin carrying a carboxyl group and which contain an active ingredient in a form fixed to these resins, and wherein the water solubilities of the at least two different salts differ from one another at least by a factor of 2.

2. A controlled-release oral dosage formulation according to claim 1, wherein the active ingredient is selected from the group consisting of salt-forming, pharmaceutically active ingredients, vitamins, minerals, nutrients and diagnostic agents.

3. A controlled-release oral dosage formulation according to claim 2, wherein the active ingredient is a salt-forming pharmaceutically active ingredient.

4. A controlled-release oral dosage formulation according to claim 3, wherein the active ingredient is selected from the group consisting of analgesics, anti-infectives and neuroleptics.

5. A controlled-release oral dosage formulation according to claim 4, wherein the analgesic is selected from the group consisting of salt-forming opioids, compounds with opioid action and non-steroidal analgesics.

6. A controlled-release oral dosage formulation according to claim 5, wherein the analgesic is selected from the group consisting of brifentanil, carfentanil, fentatienil, lofentanil, ocfentanil, trefentanil, codeine, dextropropoxyphene, dihydrocodeine, diphenoxylate, meptazinol, nalbuphine, pethidine, meperidine, tilidine, tramadol, viminol, butorphanol, dextromoramide, dezocine, diacetylmorphine, heroin, hydrocodone, hydromorphone, ketobemidone, levomethadone, levomethadyl, levorphanol, morphine, nalorphine, oxycodone, pentazocine, piritramide, alfentanil, buprenorphine, etorphine, fentanyl, remifentanil and sufentanil.

7. A controlled-release oral dosage formulation according to claim 6, wherein the analgesic is tramadol or morphine.

8. A controlled-release oral dosage formulation according to claim 4, wherein the salt-forming neuroleptic is promethazine.

9. A controlled-release oral dosage formulation according to claim 1, wherein the at least two salts of the active ingredient are selected from the group consisting of chloride, bromide, sulfate, sulfonate, phosphate, tartrate, theoclate, embonate, formiate, acetate, propionate, benzoate, oxalate, succinate, citrate, diclofenacate, naproxenate, salicylate, acetylsalicylate, glutamate, fumarate, aspartate, glutarate, stearate, butyrate, malonate, lactate, mesylate, saccharinate, cyclamate and acesulfamate salts.

10. A controlled-release oral dosage formulation according to claim 9, wherein the at least two salts of the active ingredient are selected from the group consisting of chloride, sulfate, saccharinate, theoclate, embonate, diclofenacate, naproxenate and salicylate salts.

11. A controlled-release oral dosage formulation according to claim 1, wherein the active ingredient salt is an alkali metal salt, alkaline-earth metal salt, ammonium salt, iron salt or aluminum salt.

12. A controlled-release oral dosage formulation according to claim 11, wherein the active ingredient salt is a sodium or potassium salt.

13. A controlled-release oral dosage formulation according to claim 1, wherein the dosage formulation is tablets, chewable tablets, chewing gums, coated tablets, or powders.

14. A controlled-releae oral dosage formulation according to claim 13, wherein the dosage formulation is filled into capsules.

15. A controlled-release oral dosage formulation according to claim 1, wherein the dosage formulation is tablets.

16. A controlled-release oral dosage formulation according to claim 1, wherein the dosage formulation is in multi-particulate form.

17. A controlled-release oral dosage formulation according to claim 16, wherein the dosage formulation is in the form of microparticles, micro-tablets, microcapsules, granulates, active-substance crystals or pellets.

18. A controlled-release oral dosage formulation according to claim 17, wherein the dosage formulation is in the form of micro-tablets, granulates or pellets.

19. A controlled-release oral dosage formulation according to claim 16, wherein the dosage formulation is filled into capsules or compressed into tablets.

20. A controlled-release oral dosage formulation according to claim 18, wherein the granulates or pellets have a size within the range of 0.1 to 3 mm.

21. A controlled-release oral dosage formulation according to claim 20, wherein the granulates or pellets have a size within the range of 0.5 to 2 mm.

22. A controlled-release oral dosage formulation according to claim 17, wherein the micro-tablets have a diameter of 0.5 to 5 mm.

23. A controlled-release oral dosage formulation according to claim 22, wherein the micro-tablets have a diameter of 1 to 3 mm.

24. A controlled-release oral dosage formulation according to claim 23, wherein the micro-tablets have a diameter 1 to 2 mm.

25. A controlled-release oral dosage formulation according to claim 17, wherein the active-substance crystals, micro-particles, micro-pellets or micro-capsules have a diameter of 10 μm to 1 mm.

26. A controlled-release oral dosage formulation according to claim 25, wherein the active-substance crystals, micro-particles, micro-pellets or micro-capsules have a diameter of 15 μm to 0.5 mm.

27. A controlled-release oral dosage formulation according to claim 26, wherein the active-substance crystals, micro-particles, micro-pellets or micro-capsules have a diameter of 30 μm to 200 μm.

28. A controlled-release oral dosage formulation according to claim 1, wherein at least one of the at least two salts of the active ingredient is in a sustained-release formulation.

29. A controlled-release oral dosage formulation according to claim 28, wherein all of the salts of the active ingredient are in a sustained-release formulation.

30. A controlled-release oral dosage formulation according to claim 28, wherein the sustained-release formulation is achieved by a retarding coating, or by embedding the active ingredient in a retarding matrix, or both.

31. A controlled-release oral dosage formulation according to claim 28, wherein the retarding coating is based on (1) a water-insoluble, modified, natural or synthetic polymer, (2) natural, semi-synthetic or synthetic wax, (3) natural, semi-synthetic or synthetic fat, (3) natural, semi-synthetic or synthetic fatty alcohol, or (4) a mixture of at least two of (1), (2) and (3).

32. A controlled-release oral dosage formulation according to claim 31, wherein the retarding coating further comprises a conventional softener.

33. A controlled-release oral dosage formulation according to claim 31, wherein the water-insoluble polymer is a poly (meth)acrylate, a poly(meth)acrylate copolymer, or a mixture thereof.

34. A controlled-release oral dosage formulation according to claim 33, wherein the poly(meth)acrylate is poly($C_{1-4}$)-alkyl(meth)acrylate or poly($C_1$-4)-dialkylamino-($C_1$-4)-alkyl(meth)acrylate.

35. A controlled-release oral dosage formulation according to claim 33, wherein the poly(meth)acrylate copolymer is ethylacrylate/methylmethacrylate-copolymer with a molar ratio of the monomers of 2:1, ethylacrylate/methylmethacrylate/trimethylammonium ethylmethacrylate-chloride-copolymer with a molar ratio of the monomers of 1:2:0.1, or ethylacrylate/methylmethacrylate/trimethylammonium ethylmethacrylate-chloride-copolymer with a molar ratio of the monomers of 1:2:0.2.

36. A controlled-release oral dosage formulation according to claim 31, wherein the water-insoluble polymer is a cellulose derivative.

37. A controlled-release oral dosage formulation according to claim 36, wherein the cellulose derivative is alkyl cellulose or cellulose ester.

38. A controlled-release oral dosage formulation according to claim 37 wherein the alkyl cellulose is ethyl cellulose.

39. A controlled-release oral dosage formulation according to claim 37, wherein the cellulose ester is cellulose acetate.

40. A controlled-release oral dosage formulation according to claim 33, wherein the water-insoluble polymer is applied from an aqueous medium.

41. A controlled-release oral dosage formulation according to claim 40, wherein the aqueous medium is aqueous latex or pseudo-latex dispersion.

42. A controlled-release oral dosage formulation according to claim 31, wherein the water-insoluble polymer is a mixture of polyvinyl acetate and polyvinyl pyrrolidone.

43. A controlled-release oral dosage formulation according to claim 42, wherein the mixture of polyvinyl acetate and polyvinyl pyrrolidone is in the form of an aqueous pseudo-latex dispersion.

44. A controlled-release oral dosage formulation according to claim 31, wherein the retarding coating is based on carnauba wax, beeswax, glycerine monostearate, glycerine monobehenate, glycerine ditripalmitostearate, or microcrystalline wax, or a mixture of at least two thereof.

45. A controlled-release oral dosage formulation according to claim 33, wherein the coating material further comprises a conventional softener.

46. A controlled-release oral dosage formulation according to claim 45, wherein the conventional softener is selected from the group consisting of a lipophilic diester of a $C_6$-$C_{40}$ aliphatic or aromatic dicarboxylic acid and a $C_1$-$C_8$ aliphatic alcohol, a hydrophilic or lipophilic ester of citric acid, a polyethylene glycol, a propylene glycol, an ester of glycerine, oleic acid or a mixture of at least two thereof.

47. A controlled-release oral dosage formulation according to claim 46, wherein the lipophilic diester of a $C_6$-$C_{40}$ aliphatic or aromatic dicarboxylic acid and a $C_1$-$C_8$ aliphatic alcohol is dibutylphthalate, diethylphthalate, dibutyl sebacate or diethyl sebacate.

48. A controlled-release oral dosage formulation according to claim 46, wherein the hydrophilic or lipophilic ester of citric acid is triethyl citrate, tributyl citrate, acetyltributyl citrate or acetyltriethyl citrate.

49. A controlled-release oral dosage formulation according to claim 46, wherein the ester of glycerine is triacetin, an acetylated mono- and digylceride or a mid-chain trigylceride.

50. A controlled-release oral dosage formulation according to claim 45, wherein the softener is present in quantities of 5 to 50 wt. % relative to the polymer coating material.

51. A controlled-release oral dosage formulation according to claim 50, wherein the softener is present in quantities of 10 to 40 wt. % relative to the polymer coating material.

52. A controlled-release oral dosage formulation according to claim 51, wherein the softener is present in quantities of 10 to 30 wt. % relative to the polymer coating material.

53. A controlled-release oral dosage formulation according to claim 30, wherein the retarding matrix is based upon a hydrophilic matrix material.

54. A controlled-release oral dosage formulation according to claim 53, wherein the hydrophilic material is a hydrophilic polymer.

55. A controlled-release oral dosage formulation according to claim 54, wherein the hydrophilic polymer is at least one of the group consisting of a cellulose ether, a cellulose ester and acrylic resins.

56. A controlled-release oral dosage formulation according to claim 55, wherein the hydrophilic polymer is at least one selected from the group consisting of ethyl cellulose, hydroxypropylmethyl cellulose, hydroxypropyl cellulose, hydroxymethyl cellulose, poly(meth)acrylic acid and their salts, amides and esters.

57. A controlled-release oral dosage formulation according to claim 30, wherein the coating matrix is based on a hydrophobic matrix material.

58. A controlled-release oral dosage formulation according to claim 57, wherein the hydrophobic material is selected from the group consisting of hydrophobic polymers, waxes, fats, long-chained fatty acids, their corresponding esters, their corresponding ethers, and their mixtures.

59. A controlled-release oral dosage formulation according to claim 58, wherein the hydrophobic material is selected from the group consisting of mono- or di-glycerides of $C_{12}$-$C_{30}$ fatty acids, $C_{12}$-$C_{30}$ fatty alcohols, waxes and mixtures thereof.

60. A controlled-release oral dosage formulation according to claim 1, further comprising a protective coating.

61. A controlled-release oral dosage formulation according to claim 60, wherein the protective coating is a gastric juice-resistant protective coating.

62. A controlled-release oral dosage formulation according to claim 61, wherein the gastric juice-resistant coating comprises a methacrylic acid/methylmethacrylate copolymer with a molar ratio of the monomers of 1:1, a methacrylic acid/methylmethacrylate copolymer with a molar ratio of the monomers of 1:2, a methacrylic acid/ethylacrylate copolymer with a molar ratio of the monomers of 1:1, a methacrylic acid/methylacrylate/ methylmethacrylate with a molar relationship of the monomers of 7:3:1, shellac, hydroxypropylmethyl cellulose acetate succinate, and cellulose acetate phthalate, or a mixture of at least two thereof.

63. A controlled-release oral dosage formulation according to claim 62, wherein the gastric juice-resistant coating further comprises a poly(meth)acrylate.

64. A controlled-release oral dosage formulation according to claim 63, wherein the poly(meth)acrylate is at least one of the group consisting of an ethylacrylate/methylmethacrylate-copolymer with a molar ratio of the monomers of 2:1, an ethylacrylate/methylmethacrylate/trimethylammonium ethylmethacrylate-chloride-copolymer with a molar ratio of the monomers of 1:2:0.1, or an ethylacrylate/methylmethacrylate/trimethylammonium ethylmethacrylate-chloride-copolymer with a molar ratio of the monomers of 1:2:0.2.

65. A controlled-release oral dosage formulation according to claim 1, the formulation is prepared by a process comprising producing a mixture by mixing at least two different salts of the active ingredient, the salts having a different in-vitro release rate, formulating the mixture, and coating the mixture with a protective coating.

\* \* \* \* \*

UNITED STATES PATENT AND TRADEMARK OFFICE
CERTIFICATE OF CORRECTION

PATENT NO.      : 7,572,463 B2                                    Page 1 of 1
APPLICATION NO. : 10/084674
DATED           : August 11, 2009
INVENTOR(S)     : Bartholomaeus et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 585 days.

Signed and Sealed this

Fourteenth Day of December, 2010

David J. Kappos
*Director of the United States Patent and Trademark Office*